United States Patent [19]

Pilgram

[11] 4,174,958
[45] Nov. 20, 1979

[54] ANILIDE DERIVATIVE HERBICIDES

[75] Inventor: Kurt H. G. Pilgram, Modesto, Calif.

[73] Assignee: Shell Oil Company, Houston, Tex.

[21] Appl. No.: 942,522

[22] Filed: Sep. 15, 1978

Related U.S. Application Data

[63] Continuation-in-part of Ser. No. 867,748, Jan. 9, 1978, abandoned.

[51] Int. Cl.² .................. A01N 9/22; C07D 271/10
[52] U.S. Cl. ............................. 71/88; 71/92; 548/144; 548/231; 548/221; 548/302; 548/305; 548/320
[58] Field of Search .................. 548/301; 260/307 C, 260/307 G; 71/88, 92

[56] References Cited

U.S. PATENT DOCUMENTS 2,856,277  10/1958  Bluestone et al. .......... 260/307 C
3,284,447  11/1966  Kusuda et al. ............ 548/301

Primary Examiner—Jose Tovar

[57] ABSTRACT

New herbicidally active compounds have the formula

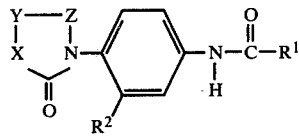

wherein $R^1$ is H, alkyl, alkenyl, cycloalkyl, $R^2$ is $CF_3$, $NO_2$, CN, halogen, alkyl, alkoxy or alkyl, and —X—Y—Z— is

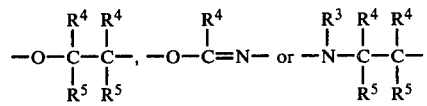

in which $R^3$ is H, or alkyl, $R^4$ is H, alkyl or cycloalkyl, $R^5$ is H or alkyl or when —Y—Z— contains two vicinal $R^4$ groups then these $R^4$ groups taken together with the ring carbon atoms to which they are attached form a saturated or unsaturated hydrocarbyl ring containing 5 or 6 carbon atoms.

11 Claims, No Drawings

ANILIDE DERIVATIVE HERBICIDES

CROSS-REFERENCE TO RELATED APPLICATIONS

This application is a continuation-in-part of Ser. No. 867,748, filed Jan. 9, 1978 now abandoned.

FIELD OF THE INVENTION

This invention relates to certain heterocyclic-substituted anilide derivatives, their use as herbicides and to herbicidal compositions containing these anilide derivatives.

SUMMARY OF THE INVENTION

The present invention is directed to a new class of compounds useful to control plant growth. The compounds have the formula I

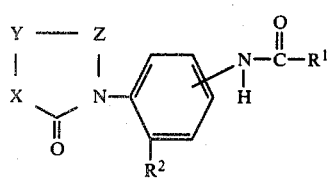

wherein $R^1$ is a hydrogen atom, an alkyl group containing 1 to 4 carbon atoms or an alkenyl group of 2 to 3 carbon atoms each optionally substituted by one or more halogen atoms having an atomic number of from 9 to 35, inclusive, or an optionally substituted cycloalkyl group containing from 3 to 5 ring carbon atoms and a total of 3 to 6 carbon atoms;

$R^2$ is $CF_3$, $NO_2$, a halogen atom having an atomic number of from 9 to 35, inclusive, an alkyl, alkoxy or alkylthio group containing from 1 to 6 carbon atoms or CN;

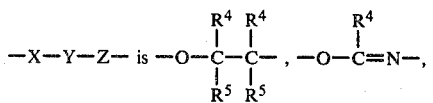

in which $R^3$ is independently a hydrogen atom or an alkyl group containing from 1 to 6 carbon atoms; each $R^4$ is independently a hydrogen atom, an alkyl group containing from 1 to 6 carbon atoms optionally substituted by one or more halogen atoms or a cycloalkyl group containing from 3 to 5 ring carbon atoms and a total of 3 to 6 carbon atoms; and each $R^5$ is independently a hydrogen atom or an alkyl group containing from 1 to 2 carbon atoms or when —X—Y— or —Y—Z— contain two vicinal $R^4$ groups then these $R^4$ groups taken together with the ring carbon atoms to which they are attached form a saturated or unsaturated hydrocarbyl ring containing 5 or 6 carbon atoms.

Because of their herbicidal properties a preferred subclass of compounds are those of formula I wherein $R^1$ is hydrogen, an alkyl group of 1 to 4 carbon atoms or alkenyl of 2 to 3 carbon atoms, e.g., methyl, ethyl, 2-propen-2-yl or the like, or optionally substituted cyclopropyl group of the formula

wherein $R^7$ is a hydrogen atom, methyl, methoxy or a halogen atom having an atomic number of from 9 to 35, inclusive, for example fluorine, chlorine or bromine. Compounds wherein $R^7$ is hydrogen, or methyl have been found to have very useful herbicidal properties, with the methylsubstituted derivatives being especially desirable as a subclass. Compounds wherein

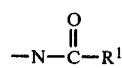

is located in the meta- or para-position relative to the heterocyclic group are generally the preferred subclasses.

Also preferred because of their herbicidal properties are the compounds of formula I wherein $R^2$ is $CF_3$, methyl, chloro or bromo.

Also preferred because of their herbicidal properties or ease of preparation are those compounds of formula I in which in the unit —X—Y—Z— the substituents on the carbon and nitrogen atoms independently are: $R^3$ is a hydrogen atom or an alkyl group containing from 1 to 4 carbon atoms, $R^4$ is a hydrogen atom, an alkyl group containing from 1 to 4 carbon atoms, cyclopropyl or 1-methylcyclopropyl and $R^5$ is hydrogen or methyl or when —X—Y— or —Y—Z— contain two vicinal $R^4$ groups then these $R^4$ groups taken together with the ring carbon atom to which they are attached can form a saturated or unsaturated hydrocarbyl ring containing 5 or 6 carbon atoms. For example, $R^3$ is hydrogen or methyl, $R^4$ is hydrogen, tertiary-butyl, methyl, cyclopropyl or 1-methylcyclopropyl and $R^5$ is hydrogen or methyl. When X—Y—Z is

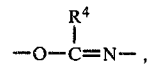

then $R^4$ is preferably 1-methylcyclopropyl, 2,2-dimethyl-propyl, or tertiary-butyl. When X—Y—Z is

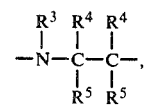

then $R^3$ is preferably methyl or ethyl and each of $R^4$ and $R^5$ is hydrogen. When X—Y—Z is

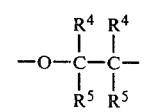

the $R^4$ on the carbon atom adjacent to the oxygen is hydrogen or methyl and each of the remaining of $R^4$ and $R^5$ is hydrogen.

Examples of species of the invention contemplated when —X—Y—Z— is

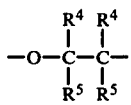

include:

N-[3-chloro-4-(2-oxo-3-oxazolidinyl)phenyl]-1-methyl-cyclopropanecarboxamide,
N-[3-chloro-4-(2-oxo-3-oxazolidinyl)phenyl]acetamide,
N-[3-chloro-4-(2-oxo-3-oxazolidinyl)phenyl]propionamide,
N-[3-bromo-4-(2-oxo-3-oxazolidinyl)phenyl]cyclopropanecarboxamide,
N-[3-chloro-4-(3,4-pentamethylene-5-oxo-1(4H)-pyrazolyl)phenyl]acetamide, and
N-[3-chloro-4-(3,4-hexamethylene-5-oxo-1(4H)-pyrazolyl)phenyl]acetamide.

Examples of species of the invention contemplated when —X—Y—Z— is

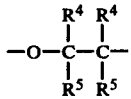

include:

N-3-chloro-4-(2-oxo-3-oxazolidinyl)phenyl-1-methylcyclopropanecarboxamide,
N-3-chloro-4-(2-oxo-3-oxazolidinyl)phenyl acetamide,
N-3-chloro-4-(2-oxo-3-oxazolidinyl)phenyl propionamide,
N-3-bromo-4-(2-oxo-3-oxazolidinyl)phenyl cyclopropanecarboxamide,
N-[3-bromo-4-(2-oxo-3-oxazolidinyl)phenyl]acetamide,
N-[3-bromo-4-(2-oxo-3-oxazolidinyl)phenyl]propionamide,
N-[3-bromo-4-(2-oxo-3-oxazolidinyl)phenyl]formamide,
N-[3-(trifluoromethyl)-4-(2-oxo-3-oxazolidinyl)phenyl]cyclopropanecarboxamide,
N-[3-(trifluoromethyl)-4-(2-oxo-3-oxazolidinyl)phenyl]acetamide,
N-[3-(trifluoromethyl)-4-(2-oxo-3-oxazolidinyl)phenyl]propionamide,
N-[3-chloro-4-(5-methyl-2-oxo-3-oxazolidinyl)phenyl]-1-methylcyclopropanecarboxamide,
N-[3-chloro-4-(5-methyl-2-oxo-3-oxazolidinyl)phenyl]cyclopropanecarboxamide,
N-[3-chloro-4-(5-methyl-2-oxo-3-oxazolidinyl)phenyl]acetamide,
N-[3-chloro-4-(5-methyl-2-oxo-3-oxazolidinyl)phenyl]propionamide,
N-[3-(trifluoromethyl)-4-(5-methyl-2-oxo-3-oxazolidinyl)phenyl]-1-methylcyclopropanecarboxamide,
N-[3-(trifluoromethyl)-4-(5-methyl-2-oxo-3-oxazolidinyl)phenyl]cyclopropanecarboxamide,
N-[3-(trifluoromethyl)-4-(5-methyl-2-oxo-3-oxazolidinyl)phenyl]formamide,
N-[3-(trifluoromethyl)-4-(5-methyl-2-oxo-3-oxazolidinyl)phenyl]acetamide, and
N-[3-(trifluoromethyl)-4-(5-methyl-2-oxo-3-oxazolidinyl)phenyl]propionamide.

Examples of species of the invention contemplated when —X—Y—Z— is

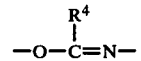

include:

N-[3-chloro-4-(2-(tert-butyl)-5-oxo-$\Delta^2$-1,3,4-oxadiazolin-4-yl)phenyl]propiolamide,
N-[3-chloro-4-(2-tert-butyl)-5-oxo-$\Delta^2$-1,3,4-oxadiazolin-4-yl)phenyl]-2-bromoacrylamide,
N-[3-bromo-4-(2-tert-butyl)-5-oxo-$\Delta^2$-1,3,4-oxadiazolin-4-yl)phenyl]isobutylamide,
N-[3-chloro-4-(2-tert-butyl)-5-oxo-$\Delta^2$-1,3,4-oxadiazolin-4-yl)phenyl]methacrylamide,
N-[3-chloro-4-(2-(tert-butyl)-5-oxo-$\Delta^2$-1,3,4-oxadiazolin-4-yl)phenyl]chloroacetamide,
N-[3-chloro-4-(2-(tert-butyl)-5-oxo-$\Delta^2$-1,3,4-oxadiazolin-4-yl)phenyl]trifluoroacetamide,
N-[3-methyl-4-(2-(tert-butyl)-5-oxo-$\Delta^2$-1,3,4-oxadiazolin-4-yl)phenyl]-1-methylcyclopropanecarboxamide,
N-[3-methyl-4-(2-(tert-butyl)-5-oxo-$\Delta^2$-1,3,4-oxadiazolin-4-yl)phenyl]acetamide,
N-[3-bromo-4-(2-tert-butyl)-5-oxo-$\Delta^2$-1,3,4-oxadiazolin-4-yl)phenyl]propionamide, and
N-[3-chloro-4-(2-tert-butyl)-5-oxo-$\Delta^2$-1,3,4-oxadiazolin-4-yl)phenyl]acrylamide.

Examples of species of the invention contemplated when —X—Y—Z is

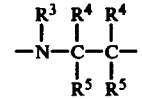

include:

N-[3-bromo-4-(3-methyl-1-oxo-1-imidazolidinyl)-phenyl]-1-methylcyclopropanecarboxamide,
N-[3-bromo-4-(2-oxo-1-imidazolidinyl)phenyl]-1-methylcyclopropanecarboxamide,
N-[3-chloro-4-(3-methyl-2-oxo-1-imidazolidinyl)-phenyl]-1-methylcyclopropanecarboxamide,
N-[3-chloro-4-(2-oxo-1-imidazolidinyl)phenyl]-1-methylcyclopropanecarboxamide,
N-[3-(trifluoromethyl)-4-(3-methyl-2-oxo-1-imidazolidinyl)phenyl]formamide,
N-[3-(trifluoromethyl)-4-(2-oxo-1-imidazolidinyl)-phenyl]-1-methylcyclopropanecarboxamide,
N-[3-bromo-4-(3-methyl-2-oxo-1-imidazolidinyl)-phenyl]cyclopropanecarboxamide,
N-[3-bromo-4-(2-oxo-1-imidazolidinyl)phenyl]cyclopropanecarboxamide,
N-[3-chloro-4-(3-methyl-2-oxo-1-imidazolidinyl)-phenyl]cyclopropanecarboxamide,
N-[3-chloro-4-(3,5-dimethyl 2-oxo-1-imidazolidinyl)-phenyl]acetamide,
N-[3-(trifluoromethyl)-4-(3-methyl-2-oxo-1-imidazolidinyl)phenyl]acetamide,
N-[3-(trifluoromethyl)-4-(2-oxo-1-imidazolidinyl)-phenyl]cyclopropanecarboxamide, N-[3-chloro-4-(3-ethyl-2-oxo-1-imidazolidinyl)phenyl]acetamide, and N-[3-bromo-4-(3-ethyl-2-oxo-1-imidazolidinyl)-3-(trifluoromethyl)phenyl]acetamide.

The compounds of the invention can be prepared according to the following general reaction scheme:

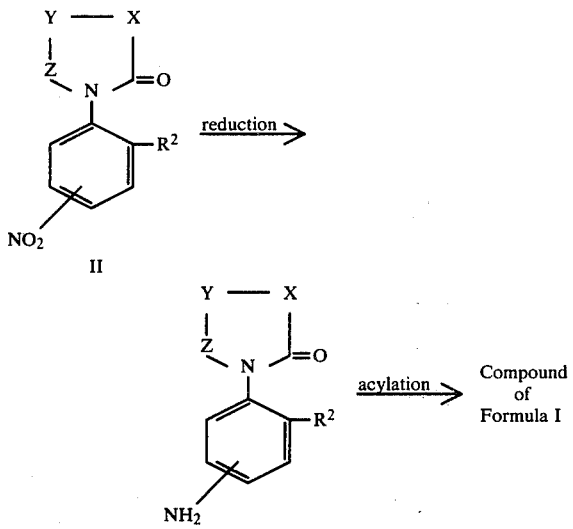

Reduction of the nitrophenyl-substituted heterocyclic compound of formula II can be carried out in the presence of known catalyst such as palladium-charcoal, Raney-nickel or the like or iron powder in refluxing water containing a small amount of acetic acid.

The resulting aminophenyl derivatives can then be acylated by methods known in the art to introduce the desired $R^1$ substituent. For example, specific carboxanilides can be prepared by treating a desired carboxylic acid chloride with the aminophenyl derivative in the presence of about one molar equivalent of triethylamine. Alternatively, the formamides are prepared by the aminophenyl derivative with 90-100% formic acid at elevated temperatures.

The substituted-phenyl-heterocyclic starting materials can be prepared by various methods. For example:

N-substituted-phenyl-2-oxazolidinones of formula II in which the unit —X—Y—Z— is —O—CH$_2$—CH$_2$— can be prepared by at least three methods: (1) by treating a beta-anilinoethanol with phosgene; (2) by treating beta-halogenoalkyl phenylcarbamates with potassium hydroxide; and (3) by reaction of 1-chloro-2-substituted-4-nitrobenzene with 2-oxazolidinone in the presence of about one molar equivalent of strong base, such as sodium hydride, in a solvent, such as dimethylformamide. The first two methods as well as the preparation of 2-oxazolidinone itself are described in J. W. Cornforth, "Heterocyclic Compounds", Vol 5, Ch 5, R. C. Elderfield, ed., John Wiley, New York, N.Y., pages 396 and 398.

3-substituted-phenyl-1,3,4-oxadiazol-2(3H)-ones of formula II in which the unit —X—Y—Z— is

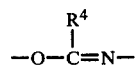

can be prepared by various methods: (1) by treating a phenylhydrazide with phosgene; (2) by nitrating (3-(3-substituted-phenyl)-1,3,4-oxadiazol-2-(3H)-ones; and (3) by treating 1,3,4-oxadiazol-2(3H)-ones with a 4-nitrohalobenzene in the presence of a strong base such as sodium hydride in dimethylformamide. The first method, described in (a) E. Hoggarth, "Chemistry of Carbon Compounds", E. Rodd., ed., Vol 4A, Ch 6, page 471, Elsevier, London (1957); (b) J. H. Boyer, "Heterocyclic Compounds", R. C. Elderfield, ed., Vol 7, page 528, Wiley, New York, N.Y. (1961); (c) L. C. Behr, "The Chemistry of Heterocyclic Compounds", A. Weissberger, ed., Vol 7, Ch 10, page 274, Interscience Publ., New York, N.Y. (1962); and (d) R. Boesch and J. Metivier, Belgian Pat. No. 657,037, Chem. Abstr., 63, 1786a (1965), although the most general one, is not applicable to hydrazides in which the phenyl ring contains a trifluoromethyl or nitro group adjacent to the hydrazide group. In these instances, the ring-closure with phosgene does not take place. The second method gives mixtures containing 4-(and 5)-nitrophenyl derivatives. The applicability of the third method is dependent on the reactivity of the halogen atom in the 4-nitrohalobenzene.

1-substituted-phenyl-2-imidazolidinones of formula II in which the unit —X—Y—Z— is

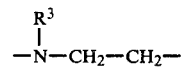

can be prepared from aryl substituted ethylenediamines and potassium cyanate followed by cyclocondensation of the intermediate urea (Gabriel and Stelzer, Ber. 28, 2929 (1895)).

Compounds of the invention further substituted by $R^3$, $R^4$ and $R^5$ as broadly defined can be prepared in a manner similar to the routes detailed above.

The compounds of the invention have been found to be useful for controlling undesirable plant growth. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important series of grasses and broadleaved weeds. Some of the compounds are particularly useful as selective herbicides for control of weeds in certain important crops.

The invention includes plant growth regulating compositions comprising a carrier or a surface-active agent, or both a carrier and a surface-active agent, and, as active ingredient, at least one compound of formula I. Likewise the invention also includes a method of controlling plant growth which comprises applying to the locus an effective amount of a compound of formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a setting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or solvent, 10-50% weight per volume toxicant, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% w toxicant, 0.5-5% w of dispersing agents, 1-5% of surface-active agent, 0.1-10% w of suspending agents such as protective colloids and thixotropic agents, 0-10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or an antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compounds of this invention comprises applying a compound of formula I, ordinarily in a composition of one of the aforementioned types, to a locus or area to be protected from undesirable plant growth such as the foliage of the plants or the plant growth medium, e.g., soil in which the plant is growing or is to be grown. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identities of compounds, intermediates and final, were confirmed by elemental analysis, and infrared and nuclear magnetic spectral analyses as necessary. The examples are for the purpose of illustration only and should not be regarded as limiting the invention in any way.

EXAMPLE 1

N-[3-chloro-4-(2-(1-methylcyclopropyl)-5-oxo-$\Delta^2$-1,3,4-oxadiazolin-yl)phenyl]-1-methylcyclopropanecarboxamide (a) 5-(1-Methylcyclopropyl)-1,3,4-oxadiazol-2(3H)-one.

A solution containing 54.0 g (0.385 mol) of 1-methylcyclopropanecarboxylic acid hydrazide (m.p. 72°-74°) and 90 g (0.9 mol) of phosgene in 1000 ml of ethyl acetate was refluxed for 2 hours. The reaction mixture was concentrated on a rotary evaporator. The residual solid crystallized from ether-hexane (1:5) to give 56.0 g (85%) of product as a white crystalline solid; m.p. 77°-78°.

(b) 3-(2-chloro-4-nitrophenyl)-5-(1-methylcyclopropyl)-1,3,4-oxadiazol-2(3H)-one.

A mixture containing 16.3 g (0.116 mol) of 1(a) and 22.4 g (0.116 mol) of 1,2-dichloro-4-nitrobenzene in 250 ml of dimethylformamide was stirred during the portionwise addition of 4.9 g (0.116 mol) of 57% sodium hydride-oil paste. After 0.5 hour, the mixture was heated at 130° for 1.5 hours, cooled and poured into ice water. The aqueous layer was acidified with hydrochloric acid and extracted with ether. Concentration of the dried ether extract followed by purification using silica chromatography gave 21.5 g (62.5%) of product as a light yellow crystalline solid; m.p. 95°-97° C. (from ether).

(c) 3-(4-amino-2-chlorophenyl)-5-(1-methylcyclopropyl)-1,3,4-oxadiazol-2(3H)-one.

A mixture containing 19 g (0.064 mol) of 1(b) above and 50 ml of glacial acetic acid in 950 ml of water was stirred and refluxed during portionwise addition of 20 g of iron powder. The reaction mixture was filtered while hot, and the filtrate was cooled and extracted with ether. The dried ether extract was concentrated to dryness. Crystallization of the residue from ether-hexane gave 5.5 g (32%) of product as a white crystalline solid; m.p. 195°-196° C.

(d) N-[3-chloro-4-(2-(1-methylcyclopropyl)-5-oxo-$\Delta^2$-1,3,4-oxadiazolin-)-yl)phenyl]-1-methylcyclopropanecarboxamide.

2.9 g of 1(c) above was treated with 1.0 g of 1-methylcyclopropanecarbonyl chloride in 50 ml of ether containing 1.0 g of triethylamine to give 1.4 g (54%) of product as a white solid; m.p. 130°–131° C. (from ether).

EXAMPLE 2

N-[4-(2-oxo-3-oxazolidinyl)-3-(trifluoromethyl)phenyl]-1-methylcyclopropanecarboxamide (a) 3-[4-Nitro-3-(trifluoromethyl)phenyl]-2-oxazolidinone.

To a stirred solution containing 8.7 g (0.1 mol) of 2-oxazolidinone and 22.6 g (0.1 mol) of 2-chloro-5-nitrobenzotrifluoride in 200 ml of dimethylformamide was added portionwise, at 20°–25° C., 4.2 g (0.1 mol) of 57% sodium hydride in oil. This addition was exothermic to 45° C. After 2 hours at ambient temperature, the reaction mixture was heated at 100° C. for 2 hours, poured into ice water, neutralized with hydrochloric acid and extracted with ether. The ether was dried and evaporated. The residual oil was crystallized from ether to give 3.5 g (14%) of product as a light tan solid; m.p. 112°–113° C.

(b) 3-[4-amino-3-(trifluoromethyl)phenyl]-2-oxazolidinone.

An ethanolic solution of 3.1 g (11 mmol) of 2(a) above was reduced over a palladium-charcoal catalyst in a Parr shaker to give 2.5 g (90%) of product as a white solid; m.p. 170°–171° C.

(c) N-[4-(2-oxo-3-oxazolidinyl)-3-(trifluoromethyl)phenyl]-1-methylcyclopropanecarboxamide.

A mixture containing 2.0 g (8 mmol) of 2(b) above, 2.5 g of triethylamine and 2.0 g of 1-methylcyclopropanecarbonyl chloride in 50 ml of tetrahydrofuran was refluxed for 2 hours. The reaction mixture was poured into water and extracted with ether, and the extract was dried and concentrated. Recrystallization of the residue from ether gave 2.0 g (75%) of product as a white crystalline solid; m.p. 146°–147° C.

EXAMPLE 3

N-[3-bromo-4-(2-(tert-butyl)-5-oxo-$\Delta^2$-1,3,4-oxadiazolin-yl)phenyl]acetamide (a) Pivalic acid 2-(2-bromo-4-nitrophenyl)hydrazide.

To a stirred and chilled (0°) solution containing 200 g (0.86 mol) of 2-bromo-4-nitrophenylhydrazine (m.p. 143°–145°) and 116.8 g (0.9 mol) of ethyldiisopropylamine in 1000 ml of tetrahydrofuran was added dropwise 108.5 g (0.9 mol) of pivaloyl chloride. The reaction mixture was stirred at ambient temperature for 1 hour and then concentrated to dryness under reduced pressure. The residue was treated with water, filtered and recrystallized from ethanol to give 165 g (52%) of product as a light yellow solid; m.p. 145° C.

(b) 3-(2-Bromo-4-nitrophenyl)-5-tert-butyl-1,3,4-oxadiazol-2(3H)-one.

A solution containing 160 g (0.506 mol) of 3(a) above and 198 g (2.0 mol) of phosgene in 900 ml of ethyl acetate was refluxed (60°) for 120 hours. The reaction mixture was concentrated. The residue was triturated with hexane to give 97.3 g (57%) of product as a light yellow crystalline solid; m.p. 99.5° C.

(c) 3-(2-Bromo-4-aminophenyl)-5-(tert-butyl)-1,3,4-oxadiazol-2(4H)-one.

A mixture containing 34.2 g (0.1 mol) of 3(b) above and 150 ml of glacial acetic acid in 1500 ml of water was stirred and refluxed during the portionwise addition of 80 g of iron powder. After 15 minutes, the reaction mixture was cooled (25°) and filtered. The filter cake was extracted with warm (60°) ethanol. The ethanolic extract was concentrated to about 150 ml and diluted with water to give 29.8 g (9%) of product as a white solid; m.p. 170°–172°.

(d) N-[3-bromo-4-(2-(tert-butyl)-5-oxo-$\Delta^2$-1,3,4-oxadiazolin-yl)phenyl]acetamide.

To a solution of 4.05 g (0.013 mol) of 3(c) above and 1.82 g (0.018 mol) of triethylamine in 75 ml of ether was added with stirring 1.26 g (0.016 mol) of acetyl chloride. After 15 minutes, the reaction mixture was diluted with water and acidified by the dropwise addition of hydrochloric acid. The etheral layer was separated, dried, and concentrated. Recrystallization of the residue from ether-hexane gave 3.78 g (82%) of product as a tan solid; m.p. 144°–145°.

EXAMPLE 4

N-[3-chloro-4-(2-(tert-butyl)-5-oxo-$\Delta^2$-1,3,4-oxadiazolin-4-yl)phenyl]formamide (a) Pivalic acid 2-(2-chloro-4-nitrophenyl)hydrazide.

To a stirred and chilled (0° C.) solution containing 25 g (0.133 mol) of 2-chloro-4-nitrophenylhydrazine and 18.06 g (0.14 mol) of ethyldiisopropylamine in 200 ml of tetrahydrofuran was added dropwise 16.75 g (0.139 mol) of pivaloyl chloride. The reaction mixture was briefly heated to reflux and then concentrated under reduced pressure. The residue was treated with water, filtered and dried to give 32.5 g (90% yield) of the desired product as a yellowish solid; m.p. 123° C.

(b) 3-(2-Chloro-4-nitrophenyl)-5-(tert-butyl)-1,3,4-oxadiazol-2(3H)-one.

A solution containing 94 g (0.346 mol) of 4(a) above and 99 g (1.0 mol) of phosgene in 1000 ml of ethyl acetate was refluxed for about 80 hours. The reaction mixture was evaporated to dryness. Recrystallization of the residue from ether-hexane gave 102.9 g (53% yield) of the desired product as a yellow solid; m.p. 98° C.

(c) 3-(2-Chloro-4-aminophenyl)-5-(tert-butyl)-1,3,4-oxadiazol-2(3H)-one.

A mixture containing 54.6 g (0.184 mol) of 4(b) above and 110 ml of glacial acetic acid in 1540 ml of water was stirred and refluxed during the portionwise addition of 25 g of iron powder. After about ¾ of an hour, the reaction mixture was cooled and filtered. The filter cake was extracted with ethanol at 50°–60° C. The ethanol extracts were concentrated and the residue was triturated with water to give 42.4 g (86% yield) of yellow product; m.p. 158°–159° C.

(d) N-[3-chloro-4-(2-(tert-butyl)-5-oxo-Δ²-1,3,4-oxadiazolin-4-yl)phenyl]formamide.

A solution containing 10 g (0.037 mol) of 4(c) above in 100 ml of 98–100% formic acid was refluxed for ½ hour, poured over ice water and extracted with ether. The ethereal extracts were washed well with water, dried, filtered and concentrated. The residual oil was triturated with hexane, filtered and dried to give 9.13 g (84% yield) of the desired product as a white solid; m.p. 124.5°–125.5° C.

EXAMPLE 5

N-[4-(3-methyl-2-oxo-1-imidazolinyl)-3-(trifluoromethyl)phenyl]-1-methylcyclopropanecarboxamide (a) 1-(2-Hydroxyethyl)-1-methyl-3-(4-nitro-3-(trifluoromethyl)phenyl)urea.

To a solution of 46.4 g (0.2 mol) of 4-nitro-3-(trifluoromethyl)phenyl isocyanate in 200 ml of tetrahydrofuran was added dropwise with stirring and external cooling 15.2 g (0.2 mol) of 2-(methylamino)ethanol. This addition was exothermic. The solution was concentrated under reduced pressure, washed with water, acidified with hydrochloric acid and extracted with ether. Crystallization of the ether extract gave 43.69 g (71% yield) of the desired product as a tan solid; m.p. 180°–181° C.

(b) 1-(2-Chloroethyl)-1-methyl-3-(4-nitro-2-(trifluoromethyl)phenyl)urea.

A solution containing 20 g (0.065 mol) of 5(a) above and 10 g of thionyl chloride in 200 ml of benzene was refluxed for 1.5 hours. The reaction mixture was concentrated under reduced pressure. Recrystallization from ether-hexane gave 16 g (76% yield) of the desired product as a light yellow solid; m.p. 86°–87° C.

(c) 1-Methyl-3-(4-nitro-2-(trifluoromethyl)phenyl)-2-imidazolidinone.

To a suspension of 14.5 g (0.045 mol) of 5(b) above in 100 ml of methanol was added a solution of 4 g of potassium hydroxide in 10 ml of water. The colored mixture was refluxed for about ½ hour, cooled and filtered. The filtrate was concentrated to dryness, treated with water, acidified with hydrochloric acid and filtered to gave 10 g (78% yield) of the desired product as a light yellow solid; m.p. 119°–120° C.

(d) 1-Methyl-3-(4-amino-2-(trifluoromethyl)phenyl-2-imidazolidinone.

An ethanolic solution of 8.9 g (0.031 mol) of 5(c) above was reduced in a Pan shaker over palladium-charcoal catalyst for about 3.5 hours at 50° C. to give 7.54 g (94% yield) of desired product as an off-white solid; m.p. 132°–133° C.

(e) N-[4-(3-Methyl-2-oxo-1-imidazolidinyl)-3-(trifluoromethyl)phenyl]-1-methylcyclopropanecarboxamide.

Reaction of 3.25 g (0.0125 mol) of 5(d) above with 1.52 g (0.0128 mol) of 1-methylcyclopropanecarbonyl chloride in the presence of 1.31 g (0.013 mol) of triethylamine gave 3.53 g (83% yield of desired product as a white solid; m.p. 90°–91° C.

EXAMPLES 6–37

Using procedures similar to those of Examples 1 through 5, additional anilide derivatives were prepared as shown in Table 1 below:

Table I
ANILIDE DERIVATIVE

| Example | R¹ | R² | —X—Y—Z— | % Yield | M.p., °C. |
|---|---|---|---|---|---|
| 6 | H | CF₃ | C(CH₃)₃<br>—O—C=N— | 69 | 129–130 |
| 7 | CH₃ | Cl | C(CH₃)₃<br>—O—C=N— | 42 | 154–155 |
| 8 | CH₃ | CF₃ | C(CH₃)₃<br>—O—C=N— | 73 | 110–111 |
| 9 | —C₂H₅ | CF₃ | C(CH₃)₃<br>—O—C=N— | 63 | 174–175 |
| 10 | —C₂H₅ | Cl | C(CH₃)₃<br>—O—C=N— | 84 | 161–162 |
| 11 | —C(CH₃)=CH₂ | Cl | C(CH₃)₃<br>—O—C=N— | 62 | 145–146 |
| 12 | —C(CH₃)=CH₂ | CF₃ | C(CH₃)₃<br>—O—C=N— | 45 | 169–170 |
| 13 | △ | Cl | C(CH₃)₃<br>—O—C=N— | 69 | 166–167 |

Table I-continued

| | | ANILIDE DERIVATIVE | | | |
|---|---|---|---|---|---|
| 14 |  | Br | CH₂C(CH₃)₃<br>—O—C=N— | 51 | 160–161 |
| 15 | 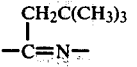<br>CH₃ | CF₃ | C(CH₃)₃<br>—O—C=N— | 76 | 157–158 |
| 16 |  | Cl | 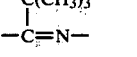—CH₃<br>—O—C=N— | 72 | 150–153 |
| 17 | <br>CH₃ | Br | CH₂C(CH₃)₃<br>—O—C=N— | 57 | 147–148 |
| 18 | <br>CH₃ | Br | C(CH₃)₃<br>—O—C=N— | 86 | 134–135 |
| 19 | <br>CH₃ | Cl | C(CH₃)₃<br>—O—C=N— | 51 | 132–133 |
| 20 | 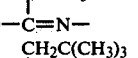<br>CH₃ | Br | —O—CH₂—CH₂— | 4 | 138–139 |
| 21 | <br>CH₃ | Cl | —O—CH₂CH₂— | 3 | 147–148 |
| 22 | 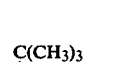<br>CH₃ | CF₃ | <br>—O— | 24 | 201–202 |
| 23 | CH₃ | CF₃ | —N(CH₃)CH₂CH₂— | 32 | 180–181 |
| 24 | 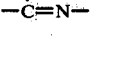 | CF₃ | —N(CH₃)CH₂CH₂— | 24 | 120–121 |
| 25 |  | Cl | —O—CH₂—CH₂— | 28 | 173–175 |
| 26 | CH₃ | Cl | —O—CH₂—CH₂— | 63 | 201–207 |
| 27 | C(CH₃) | Cl | C(CH₃)₃<br>—O—C=N— | 75 | 155–156 |
| 28 | C(CH₃) | CF₃ | C(CH₃)₃<br>—O—C=N— | 63 | 177–178 |
| 29 | 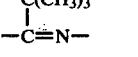<br>CH₃ | Cl | CH₃<br>—O—CH—CH₂— | 32 | 143–145 |
| 30 | —C₂H₅ | Cl | —O—CH₂—CH₂— | 32 | 158.5–159.5 |
| 31 |  | Cl | —N(CH₃)—CH₂—CH₂— | 54 | 151–153 |
| 32 | 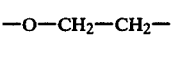 | Cl | —N(C₂H₅)—CH₂—CH₂— | 54 | 151–153 |
| 33 | <br>CH₃ | Cl | —N(C₂H₅)—CH₂—CH₂— | 53 | 128–130 |
| 34 | CH₃ | Cl | CH₃<br>—O—CH—CH₂— | 21 | 154–156 |
| 35 | 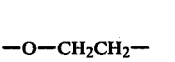 | Cl | CH₃<br>—O—CH—CH₂— | 36 | 122–125 |

Table I-continued

ANILIDE DERIVATIVE $$Y-Z\quad\quad NH-\overset{O}{\underset{\|}{C}}-R^1$$
$$\underset{X}{|}\quad\underset{N}{|}$$
$$\underset{\|}{C}$$
$$O$$
with phenyl ring bearing $R^2$

| Example | $R^1$ | $R^2$ | —X—Y—Z— | % Yield | M.p., °C. |
|---|---|---|---|---|---|
| 36 | cyclopropyl-CH₃ | Cl | C(CH₃)₃<br>—O—C=N— | 21 | 159–160 |
| 37 | CH₂ | Cl | C(CH₃)₃<br>—O—C=N— | 62 | 158–159 |

Example of Herbicidal Activity

The preemergence herbicidal activity of the compounds of the invention was evaluated by planting seeds of watergrass, garden cress, downey brome, velvet leaf, yellow foxtail, and sicklepod in test tubes, nominally measuring 25×200 millimeters, containing soil treated with the test compound at the rates of 0.1 and 1 mg per tube designated in Table I at Rates I and II, respectively. The planted soil was held under controlled conditions of temperature, moisture, and light for 11 to 12 days. The amount of germination and growth in each tube were evaluated on a 0 to 9 scale, 0 rating indicating no effect, 9 death of the seedlings or no germination.

The postemergence activity of the compounds of this invention was evaluated by spraying 7-day old crabgrass plants, 10-day old pigweed plants, 6-day old downey brome plants, 9-day old velvet leaf, 10-day old yellow foxtail plants and 7-day old sicklepod plants to runoff with a liquid formulation of the test compound at the rates of 0.8 milliliter of an 0.025% solution designated Rate I in Table I, and 0.8 milliliter of an 0.25% solution designated Rate II in Table I. The sprayed plants were held under controlled conditions for 10 to 11 days and the effect of the test compound was then evaluated visually, the results being rated on the 0 to 9 scale described above.

The results of the pre and postemergence tests are summarized in Table II.

Table II

| | HERBICIDE SCREEN RESULTS | | | | | | | | | | | | | | | | | | | | | | | |
|---|---|---|---|---|---|---|---|---|---|---|---|---|---|---|---|---|---|---|---|---|---|---|---|---|
| | Pre-emergence (Soil) | | | | | | | | | | | | Post-emergence (Foliar) | | | | | | | | | | | |
| | Water-grass | | Garden Cress | | Downey Brome | | Velvet Leaf | | Yellow Foxtail | | Sickle-pod | | Crab-grass | | Pig-weed | | Downey Brome | | Velvet Leaf | | Yellow Foxtail | | Sickle-pod | |
| Example | I | II | I | II | I | II | I | II | I | II | I | II | I | II | I | II | I | II | I | II | I | II | I | II |
| 16 | 6 | 6 | 9 | 9 | 8 | 8 | 9 | 9 | 0 | 4 | 4 | 9 | 8 | 9 | 9 | 9 | 4 | 6 | 9 | 9 | 6 | 9 | 9 | 9 |
| 1 | 5 | 6 | 9 | 9 | 5 | 6 | 9 | 9 | 0 | 2 | 4 | 8 | 8 | 9 | 9 | 9 | 4 | 8 | 9 | 9 | 7 | 9 | 9 | 9 |
| 2 | 3 | 6 | 9 | 9 | 7 | 8 | 9 | 9 | 6 | 6 | 9 | 9 | 2 | 8 | 9 | 9 | 3 | 5 | 5 | 9 | 4 | 9 | 9 | 9 |
| 15 | 0 | 0 | 7 | 7 | 5 | 5 | 8 | 9 | 0 | 0 | 0 | 0 | 7 | 7 | 9 | 9 | 7 | 7 | 9 | 9 | 9 | 9 | 6 | 6 |
| 18 | 6 | 8 | 8 | 8 | 8 | 8 | 9 | 9 | 5 | 6 | 7 | 8 | 8 | 9 | 9 | 9 | 8 | 8 | 9 | 9 | 9 | 9 | 9 | 9 |
| 17 | 0 | 0 | 6 | 7 | 7 | 7 | 7 | 7 | 0 | 0 | 0 | 0 | 8 | 9 | 9 | 9 | 7 | 9 | 9 | 9 | 9 | 9 | 9 | 9 |
| 14 | 0 | 0 | 7 | 7 | 3 | 3 | 8 | 8 | 0 | 0 | 0 | 0 | 9 | 9 | 9 | 9 | ·9 | 9 | 7 | 9 | 8 | 9 | 9 | 9 |
| 19 | 4 | 5 | 7 | 8 | 8 | 8 | 8 | 9 | 3 | 4 | 9 | 9 | 9 | 9 | 9 | 9 | 9 | 9 | 9 | 9 | 9 | 9 | 9 | 9 |
| 22 | 0 | 2 | 0 | 7 | 0 | 2 | 2 | 8 | 0 | 2 | 0 | 0 | 7 | 7 | 9 | 9 | 2 | 4 | 6 | 8 | 6 | 8 | 7 | 7 |
| 13 | 6 | 6 | 7 | 8 | 9 | 9 | 9 | 9 | 2 | 3 | 8 | 8 | 9 | 9 | 9 | 9 | 9 | 9 | 9 | 9 | 9 | 9 | 9 | 9 |
| 36 | 2 | 2 | 6 | 7 | 6 | 7 | 7 | 9 | 4 | 5 | 2 | 3 | 6 | 8 | 8 | 9 | 2 | 3 | 7 | 7 | 8 | 8 | 9 | 9 |
| 20 | 2 | 5 | 5 | 6 | 8 | 9 | 7 | 8 | 3 | 5 | 7 | 9 | 2 | 8 | 3 | 9 | 4 | 8 | 8 | 9 | 4 | 9 | 8 | 9 |
| 3 | 5 | 7 | 7 | 8 | 9 | 9 | 9 | 9 | 6 | 7 | 8 | 9 | 9 | 9 | 9 | 9 | 9 | 9 | 9 | 9 | 9 | 9 | 9 | 9 |
| 7 | 4 | 5 | 7 | 7 | 3 | 6 | 6 | 7 | 3 | 3 | 0 | 3 | 4 | 4 | 5 | 9 | 0 | 8 | 6 | 8 | 2 | 7 | 4 | 9 |
| 8 | 4 | 5 | 7 | 8 | 7 | 7 | 7 | 7 | 2 | 3 | 6 | 7 | 7 | 9 | 9 | 9 | 9 | 9 | 8 | 9 | 6 | 9 | 9 | 9 |
| 37 | 2 | 2 | 3 | 9 | 0 | 2 | 1 | 4 | 0 | 0 | 0 | 0 | 3 | 3 | 3 | 4 | 0 | 0 | 2 | 4 | 0 | 1 | 2 | 5 |

In many instances the compounds of the invention demonstrate a selective action against weeds in crop plant cultures. For example, control of grasses and broadleaf weeds in soybean and cotton crops can be achieved by postemergence application of such compounds of the invention as:

N-[3-bromo-4-(5-(tert-butyl)-2-oxo-1,3,4-oxadiazol-3(2H)-yl)phenyl]-1-methylcyclopropanecarboxamide, N-[3-(trifluoromethyl)-4-(tert-butyl)-2-oxo-1,3,4-oxadiazol-3(2H)-yl)phenyl]propanamide, N-[3-chloro-4-(tert-butyl)-2-oxo-1,3,4-oxadiazol-3(2H)-yl)phenyl]-2,2-dimethylpropaneamide.

The above species and/or other species of the invention have likewise shown postemergence, and in some cases, preemergence selective activity for crops such as peanuts, grain sorghum, cotton, rice, corn, alfalfa or the like.

I claim:

1. A compound of the formula

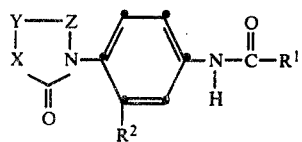

wherein $R^1$ is a hydrogen atom, an alkyl group containing 1 to 4 carbon atoms or an alkenyl group containing 2 to 3 carbon atoms or a cyclopropyl group of the formula

wherein $R^7$ is a hydrogen atom or methyl; $R^2$ is $CF_3$ bromo, chloro or methyl;

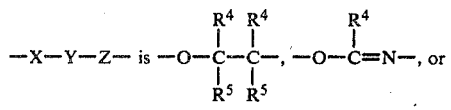

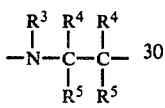

in which $R^3$ is independently a hydrogen atom or an alkyl group containing from 1 to 6 carbon atoms; each $R^4$ is independently a hydrogen atom, an alkyl group containing from 1 to 6 carbon atoms or a cycloalkyl group containing from 3 to 5 ring carbon atoms and a total of 3 to 6 carbon atoms, and each $R^5$ is independently a hydrogen atom or an alkyl group containing from 1 to 2 carbon atoms.

2. A compound according to claim 1 wherein $R^1$ is methyl, ethyl, tertiary-butyl, cyclopropyl or 1-methylcyclopropyl.

3. A compound according to claim 2 wherein $R^2$ is $CF_3$.

4. A compound according to claim 3 wherein $R^1$ is ethyl.

5. A compound according to claim 2 wherein $R^2$ is chloro or bromo.

6. A compound according to claim 5 wherein $R^1$ is methyl or tert-butyl.

7. A compound according to claim 1 wherein each $R^3$ is independently a hydrogen atom or an alkyl group containing from 1 to 4 carbon atoms, each $R^4$ is independently a hydrogen atom, an alkyl group containing from 1 to 4 carbon atoms, cyclopropyl or 1-methylcyclopropyl, and each $R^5$ is independently a hydrogen or methyl.

8. An herbicidal composition comprising an herbicidally effective amount of a compound according to claim 1 and at least one surface-active agent or carrier therefore.

9. A method for controlling undesirable plant growth at a locus to be protected which comprises applying to the locus to be protected a herbicidally effective amount of a compound according to claim 1 or a composition thereof.

10. A compound according to claim 5 wherein —X—Y—Z— is

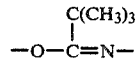

$R^1$ is cyclopropyl and $R^2$ is chloro.

11. A compound according to claim 5 wherein —X—Y—Z— is

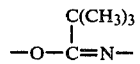

$R^1$ is methyl and $R^2$ is chloro.

* * * * *